(12) United States Patent
Kumar

(10) Patent No.: US 9,040,581 B1
(45) Date of Patent: May 26, 2015

(54) METHODS OF TREATMENT USING D-SERINE

(71) Applicant: The Florida State University Research Foundation, Inc., Tallahassee, FL (US)

(72) Inventor: Sanjay Kumar, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 14/185,421

(22) Filed: Feb. 20, 2014

Related U.S. Application Data

(60) Provisional application No. 61/767,309, filed on Feb. 21, 2013.

(51) Int. Cl.
*A61K 31/195* (2006.01)
*A61K 31/198* (2006.01)

(52) U.S. Cl.
CPC .................................... *A61K 31/198* (2013.01)

(58) Field of Classification Search
CPC ................................................... A61K 31/198
USPC ......................................................... 514/561
See application file for complete search history.

(56) References Cited

U.S. PATENT DOCUMENTS

| | | | |
|---|---|---|---|
| 6,310,097 B1 * | 10/2001 | Mitoma et al. | ................ 514/561 |
| 8,404,721 B2 | 3/2013 | Donello et al. | |
| 8,492,418 B2 | 7/2013 | Woods | |
| 2012/0302621 A1 | 11/2012 | Foster et al. | |

FOREIGN PATENT DOCUMENTS

WO  WO2013170072  11/2013

OTHER PUBLICATIONS

Schuler et al., Formation of NR1/NR2 and NR1/NR3 Heterodimers Constitutes the Initial Step in N-Methyl-D-aspartate Receptor Assembly, Journal of Biological Chemistry, vol. 283, No. 1, pp. 37-46, Jan. 4, 2008.
Palygin et al., Distinct pharmacological and functional properties of NMDA receptors in mouse cortical astrocytes, British Journal of Pharmacology, (2011) 163, pp. 1755-1766.
Kvist et al., Structure-based discovery of antagonists for GluN3-containing N-methyl-D-aspartate receptors, Neuropharmacology, Aug. 24, 2013, pp. 1-13.
Singh et al., Modulation of seizure susceptibility n the mouse by the strychnine-insensitive glycine recognition site of the NMDA receptor/ion channel complex, Br. J. Pharmacol. (1990), 99, pp. 285-288.
Pilli et al., Triheteromeric N-Methyl-D-Aspartate Receptors Differentiate Synaptic Inputs Onto Pyramidal Neurons in Somatosensory Cortex: Involvment of the Glun3A Subunit, Neuroscience 22, (2012), pp. 75-88.
Chatterton et al., Excitatory glycine receptors containing the NR3 family of NMDA receptor subunits, Nature, vol. 415, Feb. 14, 2002, pp. 793-798.
Rauner, Triheteromeric NR1/NR2A/NR2B receptors constitute the major NMDA receptor population in adult hippocampal synapses.

\* cited by examiner

*Primary Examiner* — Kevin E Weddington
(74) *Attorney, Agent, or Firm* — Christopher M. Ramsey; GrayRobinson, P.A.

(57) ABSTRACT

Methods of treatment using D-serine to target brain cells expressing GluN3 subunit-containing triheteromeric NMDARs are disclosed. The methods include inhibiting calcium ion uptake by brain cells, treating epilepsy, and treating seizures by artificially administering D-serine.

20 Claims, 4 Drawing Sheets

■ chronic spontaneous epileptic seizures and TLE
■ seizure-free; no TLE

METHODS OF TREATMENT USING D-SERINE

CROSS-REFERENCE TO RELATED APPLICATION

This claims priority to provisional application Ser. No. 61/767,309, filed Feb. 21, 2013, which is incorporated by reference herein in its entirety

FIELD OF THE INVENTION

This disclosure relates to the field of treating neurological disorders and, more particularly, to treating neurological disorders associated with N-methyl-D-aspartate receptor activity.

BACKGROUND

N-methyl-D-aspartate receptors ("NMDARs") are receptor complexes composed of glycine-binding and glutamate-binding sunbunits. The glycine binding subunits are GluN1 and GluN3 (GluN3 A-B). The glutamate binding subunit is GluN2 (GluN2 A-D). Glycine and glutamate modulate the activity of the NMDARs. The NMDAR subunit composition determines the biological properties of these receptors.

The GluN1, GluN2, and GluN3 subunits assemble in different permutations to form NMDARs. Diheteromeric NMDARS include GluN1/GluN2 and GluN1/GluN3. Triheteromeric NMDARs include GluN1/GluN2/GluN2 and, as the inventor discovered, GluN1/GluN2/GluN3. GluN1/GluN2/GluN3 is activated when glycine and glutamate are both present. GluN1/GluN3 is activated by glycine. Activating an NMDAR opens a cation-specific ion channel, allowing ions such as $Na^+$, $K^+$, and $Ca^{2+}$ to flow into the cell.

The amino acid D-serine is an important candidate for an NMDAR-modulating drug because it is synthesized in the brain and is known to be an NMDAR agonist. Because D-serine is a known NMDAR agonist, conventional wisdom suggests that it would not also function as an NMDAR antagonist.

It would be advantageous to develop a treatment composition and treatment regimen employing an NMDAR antagonist that is highly biocompatible, not substantially neurotoxic, and is able modulate the activity of NMDARs.

SUMMARY

The methods described herein take advantage of the discovery that D-serine is an antagonist of GluN3-containing triheteromeric NMDARs. D-serine may be used to treat disorders associated with NMDAR activity, specifically the disorders that may be associated with GluN3 subunit-containing triheteromeric NMDARs.

In a first embodiment, a method of inhibiting calcium ion uptake by brain cells comprises artificially administering D-serine to brain cells expressing GluN3 subunit-containing triheteromeric NMDARs, the amount of D-serine being effective to inhibit calcium ion uptake by the cells.

In another embodiment, a method of treating epilepsy comprises artificially administering to an epileptic patient a composition comprising D-serine in an amount effective to inhibit the occurrence of epileptic seizures.

In yet another embodiment, a method of treating seizures comprises artificially administering to a patient in need of such treatment a seizure-reducing effective amount of D-serine.

These methods provide advantageous new uses for the bio-compatible amino acid D-serine.

DETAILED DESCRIPTION OF EMBODIMENTS

In the Summary and in the Detailed Description of Embodiments, reference is made to particular features. Where a particular feature is disclosed in the context of a particular aspect or embodiment, that feature can also be used, to the extent possible, in combination with and/or in the context of other aspects and embodiments.

In this section, embodiments are described more fully. These embodiments may, however, take many different forms and should not be construed as limited to those set forth herein.

Figure 1:
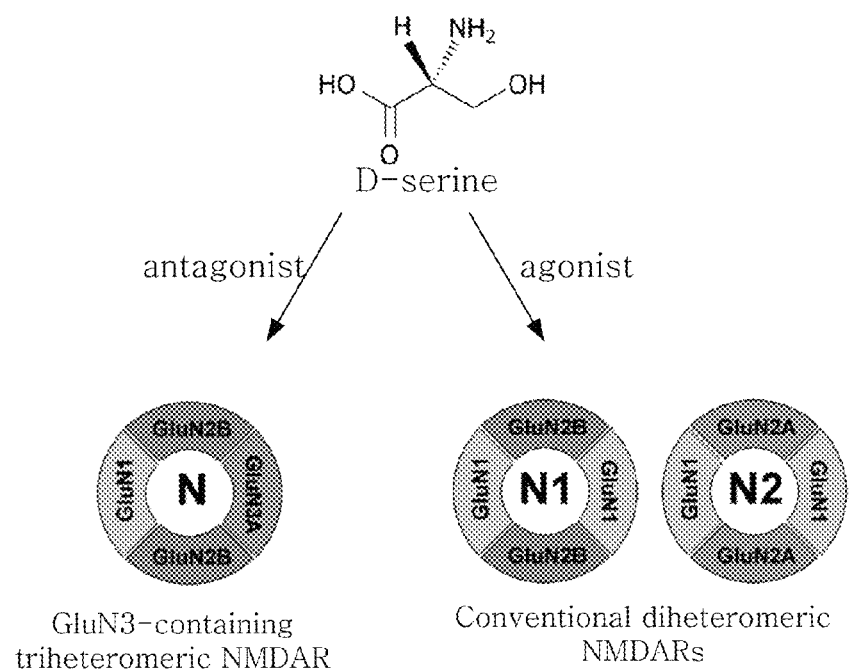
FIG. 1 is a diagram illustrating the different effect of D-serine on GluN3-containing triheteromeric NMDARs and conventional diheteromeric NMDARs.

Referring to FIG. 1, the inventor recently discovered that certain brain cells express GluN3-containing triheteromeric receptors and that D-serine is an antagonist of those receptors. This research is described in detail in J. Pilli and S. Kumar, *Neuroscience* 222:75-88 (2012), which is incorporated by reference in its entirety. This discovery is in direct contrast to the fact that D-serine is a known agonist of conventional diheteromeric NMDARs.

Targeting GluN3-containing triheteromeric receptors with D-serine provides advantageous methods of using D-serine to inhibit the activity of GluN3-containing triheteromeric receptors. One reason for this is that, as an antagonist, D-serine essentially shuts off the ion channel that these NMDARS regulate. Because GluN3-containing triheteromeric NMDARs are located in regions of the brain associated with neurological disorders such as seizures, epilepsy, and addiction, D-serine may be used to treat such neurological disorders. To "treat," as used herein, means medically treating and includes, by way of example, preventing the onset of, alleviating the severity of, and/or preventing the recurrence of, a particular pathology or symptom of the pathology.

D-serine is already produced in the brain to a certain extent, therefore, the brain may contain a small amount endogenous D-serine. In the methods that are described herein, D-serine is artificially administered to a treatment subject such as brain cells and/or a patient. A normal amount of endogenous D-serine is produced via the body's normal functions. Endogenous D-serine produced by the body behaving normally is not "artificially administered," as described below, because there is no artificial source of, or artificial stimulus for producing, D-serine.

At the outset, it is to be understood that D-serine refers to D-serine and/or its pharmaceutically acceptable salt(s).

Excitotoxicity is a process during which neuronal cells are damaged or destroyed by being overstimulated with neurotransmitters. When NMDARs are overstimulated, high levels of Ca(2+) enter the cell, triggering a chain of events that damage the cell. One way to treat neurological disorders associated with excitotoxicity is to effectively turn off NMDARs, which inhibits calcium ion uptake by the cells. Because D-serine antagonizes GluN3 subunit-containing triheteromeric NMDARs, it can be used to turn off those particular NMDARs.

In a first method, D-serine is used to inhibit calcium ion uptake by brain cells. This method includes artificially administering D-serine to brain cells expressing GluN3 subunit-containing triheteromeric NMDARs, where the amount of D-serine is effective to inhibit calcium ion uptake by the cells.

Because D-serine inhibits calcium uptake by brain cells expressing GluN3 subunit-containing triheteromeric NMDARs, D-serine may be used to treat various neurological disorders associated with excitotoxicity, including, but not limited to, addiction, epilepsy, and seizures.

In a second method, D-serine is used to treat epilepsy. This method includes artificially administering D-serine to an epileptic patient in an amount effective to inhibit the occurrence of epileptic seizures.

In a third method, D-serine is used to treat seizures, a common symptom of epilepsy. This method involves artificially administering to a patient in need of such treatment a seizure-reducing effective amount of D-serine.

In these methods, the amount effective to perform its intended function is the minimum amount that provides the intended therapeutic effect on the subject treated. In humans, an effective amount range is often 1-1,000 mg/day, including 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective.

More examples of particular effective amounts of D-serine include, but are not limited to, 1 micromole to 500 micromole, 25 micromole to 175 micromole, 50 micromole to 150 micromole, 75 micromole to 125 micromole, or about 100 micromole.

Examples of concentrations of D-serine in a D-serine composition include, but are not limited to, 1 $\mu$M to 500 $\mu$M, 25 $\mu$M to 175 $\mu$M, 50 $\mu$M to 150 $\mu$M, 75 $\mu$M to 125 $\mu$M, or about 100 $\mu$M.

The amount administered may vary depending on numerous factors, including age, weight, height, severity of the disorder, administration technique, and others. The actual amount of D-serine to be administered in a given case may be determined by a physician taking into account the relevant circumstances.

In these methods, there are many different ways that D-serine may be artificially administered to the brain cells and/or a patient. Artificial administration techniques include, but are not limited to administering one or more pharmaceutically acceptable dosage forms such as suspensions, tablets, suppositories, capsules, injectables, transdermals or the like. Other suitable artificial administration techniques include oral, sublingual, buccal, intravenous, subcutaneous, transcutaneous, intramuscular, intracutaneous, intrathecal, epidural, intraocular, intracranial, inhalation, intranasal, or the like. Yet another example of an artificial administration technique is artificially stimulating the production of D-serine within the body. Any combination of these administration techniques may also be used.

D-serine may be an active ingredient in a pharmaceutical composition. In such a case, D-serine may be blended with one or more ingredients useful for making the composition into a pharmaceutically acceptable dosage form such as a suspension, tablet, capsule, injectable, or other dosage form that comports with the artificial administration technique. Exemplary ingredients include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

In these methods, it may be advantageous to selectively contact brain cells from an area of the brain known to contain brain cells expressing GluN3 subunit-containing triheteromeric NMDARs with D-serine. Because D-serine is an agonist of conventional NMDARs, one might want to avoid activating conventional NMDARs in another area of the brain or, at least, minimize D-serine's contact with areas of the brain that do not contain brain cells expressing GluN3 subunit-containing triheteromeric NMDARs.

Selective contact of brain cells from an area of the brain known to contain brain cells expressing GluN3 subunit-containing triheteromeric NMDARs may be achieved by supplying D-serine locally such that the concentration of D-serine within that particular area of the brain is higher than the concentration of D-serine outside that particular area of the brain.

The temporal lobe, including the medial entorhinal cortex, is an area of the brain that contains brain cells expressing GluN3 subunit-containing triheteromeric NMDARs. The temporal lobe is also the source of a particular form of epilepsy called temporal lobe epilepsy. For treating epilepsy and/or seizures, it might be desirable to artificially administer D-serine by selectively contacting the patient's temporal lobe or, more particularly, the patient's medial entorhinal cortex with D-serine. A preferred selective contact technique for targeting specific areas of the brain involves injecting D-serine into or onto the targeted part of the brain. This can be accomplished by implanting the patient with a D-serine administration device such as a pump or by manual injection through a cannula positioned at the target area of the brain.

As discussed in the Examples, when D-serine is artificially administered by selectively contacting the patient's temporal lobe with D-serine, D-serine inhibits the occurrence of seizures associated with temporal lobe epilepsy, including chronic epileptic seizures. D-serine reduces the frequency of and/or substantially eliminates such seizures. One reason for this effect is that D-serine prevents excitotoxic cell loss, which is cell loss due to excitotoxicity.

EXAMPLES

This section discusses experimental research showing that D-serine antagonizes GluN3-containing triheteromeric NMDARs. These examples are provided for experimental support and do not limit the scope of what is claimed.

Example 1

D-Serine Inhibits Seizure Activity in Epileptic Rats

This example shows that D-serine, artificially administered to epileptic rats by selectively contacting the rats' medial entorhinal cortex, inhibits seizure activity and prevents neuronal cell death.

Experimental.

Male Sprague-Dawley rats weighing about 200 grams were treated with a single systemic treatment of the cholinergic muscarinic agonist pilocarpine to mimic temporal lobe epilepsy as described by Kumar and Buckmaster in *Journal of Neuroscience* 26: 4613-4623 (2006), which is incorporated by reference herein. The rats were unilaterally implanted with a brain cannula and allowed to recover for three days prior to being treated with pilocarpine. The pilocarpine dose was 380 mg/kg. Following control of status epilepticus with diazepam and a latent period, 90% of the pilocarpine treated rats developed chronic spontaneous seizures with an underlying pathology that mimicked the kind seen in human patients with temporal lobe epilepsy.

After pilocarpine treatment, a test group of rats was administered D-serine and a control group of rats was administered aCSF daily for 12 days. The first administration occurred two hours after pilocarpine treatment. The rats were video-monitored forty hours per week for frank seizure activity for the duration of the infusions.

Following the treatment regimen, the rats were euthanized and their brains removed following intra-aortal perfusion with a fixative. Horizontal brain slices 50 micrometers thick from both groups were Nissl-stained for stereological quantification of cell populations in LIII of the medial entorhinal cortex.

Results.

Figure 2:
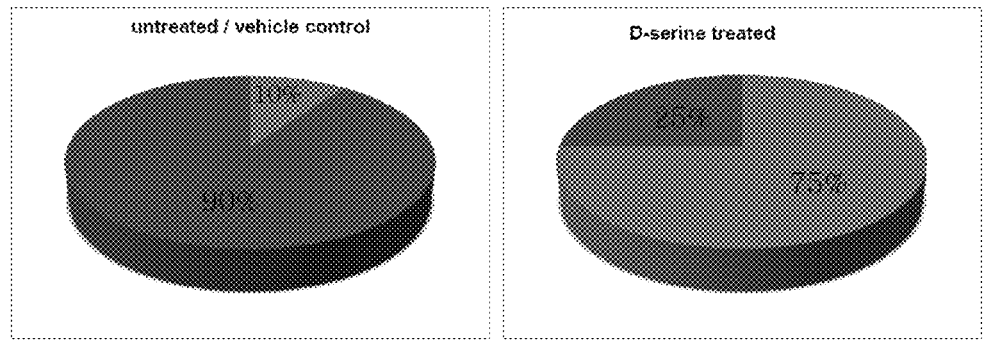
FIG. 2 is a set of pie charts showing that D-serine inhibits seizures and epilepsy in epileptic rats.

FIG. 2 is a pie chart summarizing the results of the effects of D-serine on inhibiting seizures in the rats. 90% of the rats that were not treated with D-serine had chronic epileptic seizures. 75% of the rats treated with D-serine were seizure-free, meaning D-serine prevented those rats from developing temporal lobe epilepsy during the test period. In other words, D-serine reduced the percentage of pilocarpine treated rats that developed seizures from 90% to 25%.

Figure 3:
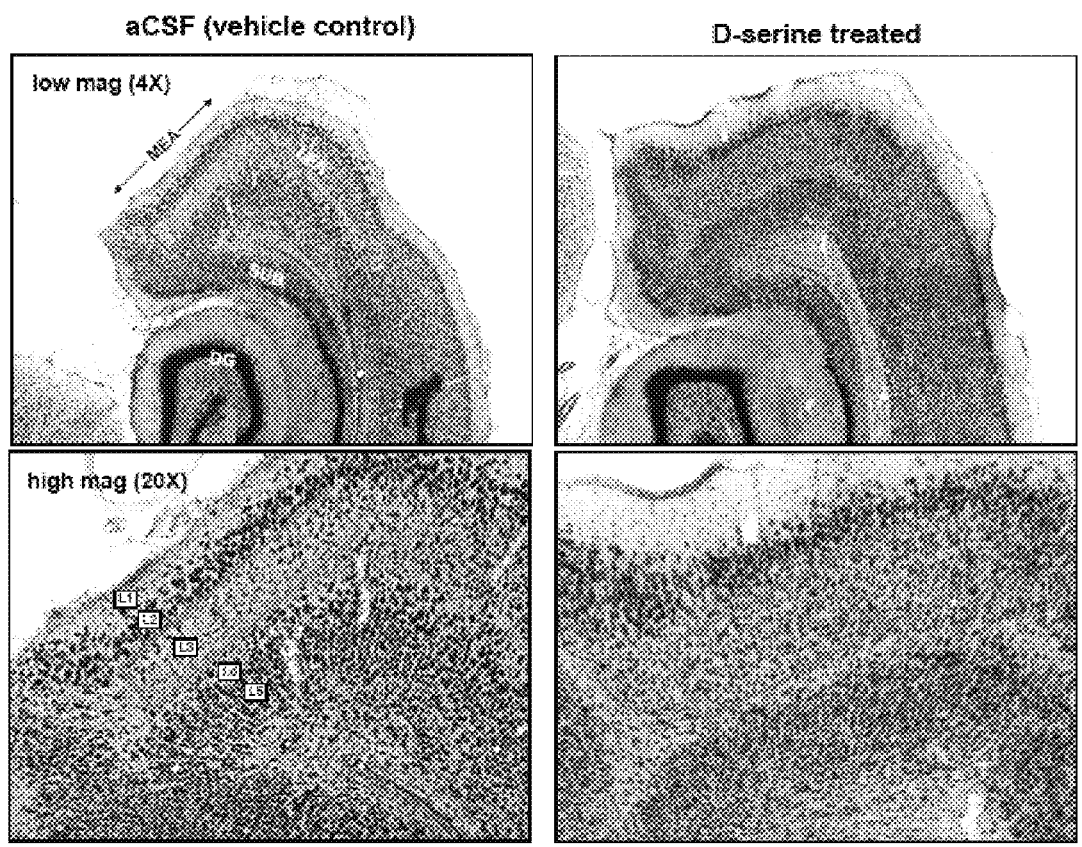
FIG. 3 is a set of micrographs showing Nissl-stained 50 micrometer thick brain sections of pilocarpine treated rats administered aCSF (vehicle control) and/or D-serine.

FIG. 3 is a series of brain slice images of the left medial entorhinal cortex (MEA) of cannulated rats. The box outlines layer LIII of the medial entorhinal cortex. DG means dentate gyrus, SUB means subiculum, LEA means lateral entorhinal area, and L refers to the layer. From the images, it is clear that treatment with D-serine prevented cell loss in LIII.

Table 1 summarizes the mean estimated cell count in LIII from the microscope images.

TABLE 1

Comparison of Cell Count in LIII

| Condition | Mean est. cell count (left + right) | # Animals |
|---|---|---|
| Naïve control | 159 ± 21 | 2 |
| Vehicle (aCSF) | 77 ± 1 | 2 |
| D-serine treated | 140 ± 10 | 3 |

These data show that D-serine prevented cell loss in LIII of the medial entorhinal cortex. D-serine was neuroprotective after pilocarpine treatment, reducing cell loss by about 80%. This also confirms that GluN3 subunit-containing triheteromeric NMDARs are involved in temporal lobe epilepsy related pathology.

Example 2

D-Serine Inhibits Calcium Uptake by GluN3-Containing Tri-Heteromeric NMDARs

Permeability to Ca(2+) is a hall-mark of the NMDA receptor. Conventional GluN1/GluN2-containing NMDARs exhibit high Ca(2+)-permeability, whereas GluN1/GluN3-containing NMDARs, alone or in combination with GluN2 subunits in heterologous expression systems, show reduced Ca(2+) permeability.

Figure 4:
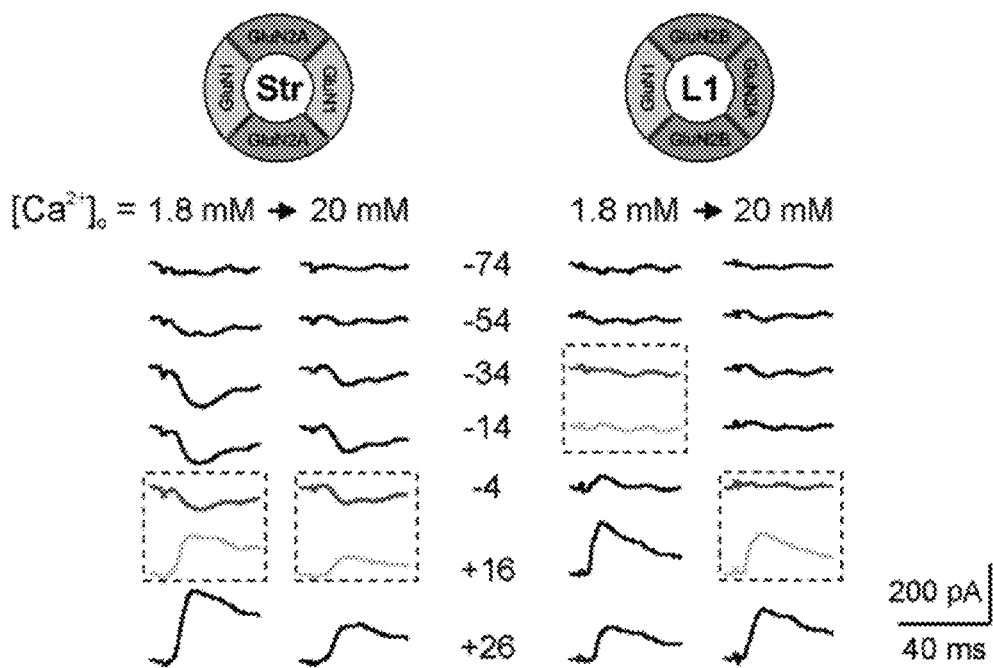
FIGS. 4 and 5 are a set of graphs showing the EPSC assessment of Ca(2+) permeability in synaptic L1 and Str inputs. The graphs in FIG. 4 show families of averaged representative traces recorded from a single neuron in response to stimulation of Str and L1 inputs at the indicated HPs (numbers in the middle are in mV) under different $[Ca2+]_0$ conditions. Hatched boxes indicate HPs where EPSCs reverse polarity ($E_{rev}$). The graph in FIG. 5 shows the mean $E_{rev}$ values, measured from I-V relationships, as a function of $[Ca2+]_0$ for the respective pathways.

The NMDARs at L1 inputs are GluN3-containing triheteromeric NMDARS, whereas the NMDARs at Str inputs are conventional diheteroemric NMDARs. To directly investigate Ca(2+)-permeability of NMDARs at L1 and Str synapses of Sprague-Dawley rats, shifts in reversal potential ($E_{rev}$) of the synaptically activated currents were measured during local perfusion of isosmotic solutions with different extracellular Ca(2+) concentrations. The results are shown in FIG. 4.

Figure 5:
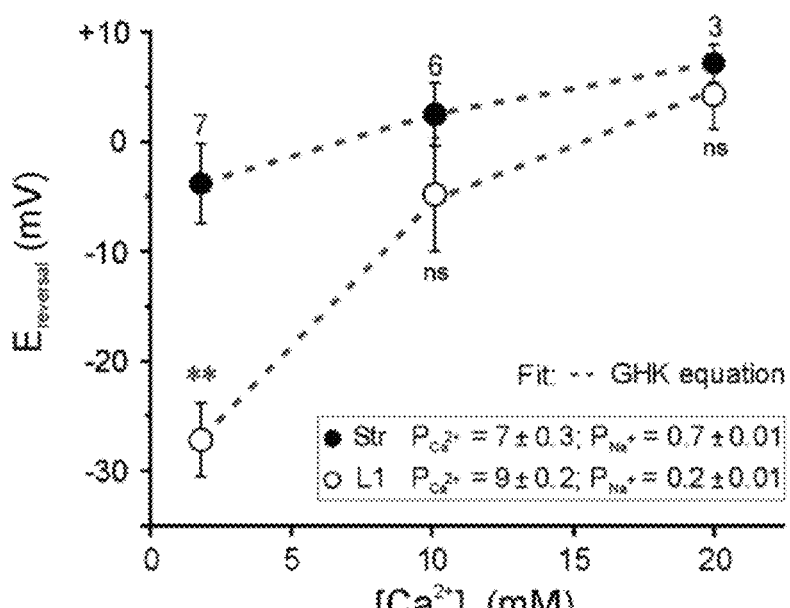

When $[Ca(2+)]_0$ was increased from 1.8 to 10 mM and subsequently to 20 mM, $E_{rev}$ either remained invariant or shifted in a positive direction for both Str and L1 inputs, thereby ruling out impermeance of these receptors to Ca(2+). The shifts in $F_{rev}$ were overall greater for L1 compared to the Str EPSCs, with maximal change occurring in L1 during transition of $[Ca(2+)]_0$ from the starting value of 1.8-10 mM as shown in FIG. 5.

These data were compared to the extended GHK constant-field equation to estimate the relative permeabilities of Ca(2+) $P_{Ca2+}$) and Na+ ($P_{Na+}$) through NMDARs at these synapses. The permeability of Na+, generally assumed to be 1 (along with $P_{K+}$), was kept a free parameter to fit the data (FIG. 5). $P_{Ca2+}$ for NMDARs at L1 inputs was similar to $P_{Ca2+}$ for NMDARs at Str inputs (9±2.9 vs. 7±1.8 respectively; p=0.6, t-test; n=6 cells). $P_{Na+}$ for the same receptors at L1 inputs was significantly smaller than $2_{Na+}$ for receptors at Str inputs (0.2±0.1 vs. 0.8±0.1 respectively; p<0.005, t-test). These data suggest that, relative to Na+, NMDARs at L1 inputs are five-fold more permeable to Ca(2+) than conventional GluN1/GluN2A-containing NMDARs at Str inputs These receptors also appear to be selective for Ca(2+).

Figure 6:
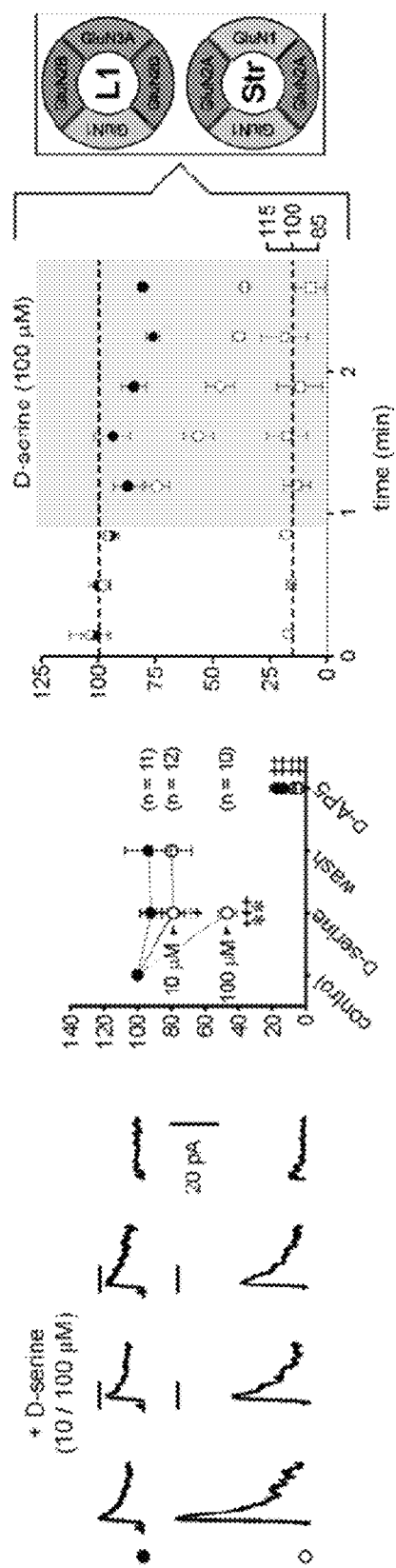
FIG. 6 is a set of graphs showing the effect of D-serine on EPSCs for L1 and Str synapses of rat brains. The left panel depicts the average consecutive records (≤10) of pure NMDAR-mediated EPSC (pharmacologically isolated in a mixture containing NBQX and picrotoxin—PTX 50 micromolar,—to block AMPA-kainite receptors and $GABA_A$-mediated inhibition) evoked in a single neuron (+30 mV) under the indicated conditions. The middle panel depicts the average percentage change in amplitude for both responses and the time course of these changes with D-serine administration times marked by the shaded region on the time plots. The right panel shows the subunit composition of the NMDARs at the L1 and Str inputs.

FIG. 6 shows the effect of D-serine on NMDAR-mediated EPSC at Str and L1 synapses. D-serine significantly suppressed L1, but not Str, EPSCs at the two concentrations tested (10 and 100 micromolar), although the suppression was greatest at the higher concentration. A small suppression of the Str response is notable, but this effect was neither consistent nor statistically significant. These data confirm pathway-specific differences in NMDAR subunit composition.

Various modifications of the embodiments described here can be made without departing from the spirit and scope of the invention as described above.

That which is claimed is:

1. A method of inhibiting calcium ion uptake by brain cells, the method comprising artificially administering D-serine to brain cells expressing GluN3 subunit-containing triheteromeric NMDARs, the amount of D-serine being effective to inhibit calcium ion uptake by the cells.

2. The method of claim 1, wherein the brain cells are from a brain's temporal lobe.

3. The method of claim 1, wherein the brain cells are from a brain's medial entorhinal cortex.

4. The method of claim 1, wherein the GluN3 subunit-containing NMDARs are triheteromeric NMDARs containing GluN1 and GluN2 in addition to GluN3.

5. The method of claim 1, wherein D-serine is artificially administered by selectively contacting brain cells from an area of the brain known to contain brain cells expressing GluN3 subunit-containing triheteromeric NMDARs.

6. The method of claim 1, wherein the brain cells are from an epileptic patient.

7. The method of claim 6, wherein the D-serine is artificially administered by selectively contacting a region of the epileptic patient's brain with the D-serine, the region being pre-identified as having cells expressing GluN3 subunit-containing triheteromeric NMDARs.

8. The method of claim 6, wherein the D-serine is artificially administered by selectively contacting a temporal lobe of the epileptic patient's brain with the D-serine.

9. The method of claim 6, wherein the D-serine is artificially administered by selectively contacting a medial entorhinal cortex of the epileptic patient's temporal lobe with the D-serine.

10. The method of claim 6, wherein the D-serine is artificially administered by injecting a temporal lobe of the patient's brain with the D-serine.

11. The method of claim 6, wherein the D-serine is artificially administered by injecting a medial entorhinal cortex of the epileptic patient's temporal lobe with the D-serine.

12. The method of claim 6, wherein the epileptic patient has temporal lobe epilepsy.

13. The method of claim 1, wherein the brain cells are from a patient that has seizures.

14. The method of claim 13, wherein D-serine is artificially administered by selectively contacting a region of the patient's brain pre-identified as having cells expressing GluN3 subunit-containing triheteromeric NMDARs with D-serine.

15. The method of claim 14, wherein D-serine is artificially administered by selectively contacting a temporal lobe of the patient's brain with D-serine.

16. The method of claim 14, wherein D-serine is artificially administered by selectively contacting a medial entorhinal cortex of the patient's temporal lobe with D-serine.

17. The method of claim 14, wherein D-serine is artificially administered by injecting a temporal lobe of the patient's brain with D-serine.

18. The method of claim 14, wherein D-serine is artificially administered by injecting a medial entorhinal cortex of the patient's temporal lobe with D-serine.

19. The method of claim 14, wherein the seizures are caused by temporal lobe epilepsy.

20. The method of claim 1, wherein the D-serine is artificially administered as a pharmaceutical dosage form comprising D-serine and at least one pharmaceutically acceptable excipient.

* * * * *